United States Patent [19]

Blackmon et al.

[11] Patent Number: 4,973,746

[45] Date of Patent: Nov. 27, 1990

[54] PROCESS FOR CONVERTING PET SCRAP TO DIAMINE MONOMERS

[75] Inventors: Kenneth P. Blackmon, Mobile, Ala.; Daniel W. Fox; Sheldon J. Shafer, both of Pittsfield, Mass.

[73] Assignee: General Electric Company, Pittsfield, Mass.

[21] Appl. No.: 261,800

[22] Filed: Oct. 24, 1988

[51] Int. Cl.$^5$ .................. C07C 253/20; C07C 227/06
[52] U.S. Cl. .................................. 562/442; 558/311; 558/313; 564/134; 564/385; 564/388
[58] Field of Search ................ 558/311, 313; 564/388; 562/442

[56] References Cited

U.S. PATENT DOCUMENTS

| | | | |
|---|---|---|---|
| 2,678,941 | 5/1954 | Ferstandig | 558/211 |
| 2,678,942 | 5/1954 | Ferstandig | 558/311 |
| 2,744,925 | 5/1956 | Toland, Jr. | 558/311 |
| 2,773,891 | 12/1956 | Toland, Jr. et al. | 558/311 |
| 2,857,416 | 10/1958 | Ferstandig et al. | 558/211 |
| 2,891,088 | 6/1959 | Condo et al. | 564/388 X |
| 2,901,504 | 8/1959 | Aries | 558/311 X |
| 2,941,954 | 6/1960 | Wilkes | 564/388 X |
| 2,970,170 | 1/1961 | Lind | 558/311 X |
| 3,069,469 | 12/1962 | Wilkes | 564/388 X |
| 3,647,054 | 3/1972 | Tsuboi et al. | 564/388 X |

FOREIGN PATENT DOCUMENTS

| | | | |
|---|---|---|---|
| 39-28638 | 12/1964 | Japan | 564/388 |
| 9133339 | 12/1974 | Japan | 564/388 |
| 0002941 | 1/1981 | Japan | 564/388 |

OTHER PUBLICATIONS

Hans G. Zengel and Manfred J. Bergfeld, A New Process for the Production of P-Phenylenediamine alternatively from Polyestrer Waste, Terephthalic Ester, or Terephthalic Acid, Ind. Eng. Chem. Prod. Res. Dev., vol. 15, No. 3, 1976, pp. 186–189.

*Primary Examiner*—Joseph Paul Brust
*Attorney, Agent, or Firm*—Spencer Conard

[57] ABSTRACT

Scrap poly(ethyleneterephthalate) is converted to useful amine and diamine monomers such as para-xylylenediamine, 1,4-bis(aminomethyl)cyclohexane and 4-aminomethyl benzoic acid for the production of various polyamides. The conversion of poly(ethyleneterephthalate) to diamine monomers is achieved by a three step process involving (a) ammonolysis of the poly(ethyleneterephthalate) to produce terephthalamide and ethylene glycol; (b) pyrolytic dehydration of the terephthalamide to produce terephthalonitrile; and (c) hydrogenation of the terephthalonitrile to produce the para-xylylene diamine and/or 1,4-bis(aminomethyl)-cyclohexane. The conversion of poly(ethyleneterephthalate) to 4-aminomethyl benzoic acid involves the steps of (a) ammonolysis of the poly(ethyleneterephthalate) to produce terephthalamide; (b) partial pyrolytic dehydration of said terephthalamide to produce 4-cyanobenzoic acid; and (c) hydrogenation of said 4-cyanobenzoic acid to produce 4-aminomethylbenzoic acid. The process of the present invention permits the conversion of low value PET scrap such as beverage bottles, fibers and film to relatively high value and relatively pure diamine monomers and ethylene glycol.

1 Claim, No Drawings

PROCESS FOR CONVERTING PET SCRAP TO DIAMINE MONOMERS

BACKGROUND OF THE INVENTION

The present invention relates to production of useful monoamine and diamine monomers from poly(ethyleneterephthalate). More particularly, it relates to the conversion of poly(ethyleneterephthalate) scrap to ethylene glycol and to useful amine functional monomers such as paraxylylenediamine, 1,4-bis (aminomethyl) cyclohexane isomers and 4-aminomethylbenzoic acid.

Poly(ethyleneterephthalate) (PET) is a thermoplastic polyester which finds commercial utility in the production of disposable consumer items such as soft drink bottles, packaging films, and fibers for fabrics and the like. These PET consumer items are eventually discarded thereby either contributing to environmental pollution as trash or finding marginal utility as PET scrap for recycle as low grade PET. Attempts at reducing the amount of PET trash have included the aforementioned recycling of PET to low grade PET. Prior recycling of PET, however, has had a number of problems associated with it including that scrap PET items are often partially degraded and have colorants therein which means that recycled PET is not colorless and thus cannot be used for many commercial applications, for example as PET stock for soft drink bottles.

Therefore, it is a principal objective of the present invention to provide a process for the conversion of scrap poly(ethyleneterephthalate) to valuable, substantially pure chemical products in high yields.

It is also an objective to provide a process for converting scrap PET to monomers useful for the production of various polyamides.

SUMMARY OF THE INVENTION

Accordingly, this invention provides a method for converting scrap poly(ethyleneterephthalate) to useful, substantially pure chemical products, including ethylene glycol, terephthalamide, terephthalonitrile, paraxylylenediamine and/or 1,4-bis(aminomethyl)cyclohexane, in high yields as primary products. Additional products may include 4-carboxybenzamide, 4-cyanobenzoic acid and 4-(aminomethyl) benzoic acid. The present process involves (1) ammonolysis of PET to produce terephthalamide, (2) pyrolytic dehydration of the terephthalamide to terephthalonitrile, and (3) standard hydrogenation of the terephthalonitrile to para-xylylenediamine and/or saturated para-xylylenediamine (1,4-bis(aminomethyl)cyclohexane). The scrap PET employed may initially include contaminates such as polyethylene bottom cups, paper labels, glues, metal caps and metal rings or the scrap PET employed may be pre-sorted from the above contaminates.

DESCRIPTION OF THE INVENTION

According to the present invention, a process for producing a diamine monomer from scrap poly(ethyleneterephthalate) involves the steps of (a) ammonolysis of the poly(ethyleneterephthalate) to produce terephthalamide; (b) pyrolytic dehydration of the terephthalamide to produce terephthalonitrile; and (c) standard hydrogenation of the terephthalonitrile to produce the diamine monomer, the diamine monomer being selected from the group consisting of paraxylylenediamine and 1,4-bis(aminomethyl)cyclohexane.

The ammonolysis of the scrap poly(ethyleneterephthalate) involves contacting the PET dispersed in ethylene glycol with ammonia and applying pressure and heat thereto whereupon the PET reacts with the ammonia to produce terephthalamide and ethylene glycol. The initial ethylene glycol provides a reaction and heat exchange media as well as partial solvent for the PET. Preferably the contacted poly(ethyleneterephthalate), ammonia, and ethylene glycol are heated to a reaction temperature of from between about 120° C. and about 180° C. and are pressurized to a reaction pressure of 125 pounds per square inch (psi) thereby resulting in a reaction which produces terephthalamide in a yield of greater than 90 percent and at a purity of greater than 99 percent. Ammonolysis may be carried out at reaction temperatures of from about 80° C. to about 250° C. At temperatures below this range, the reaction is slow and at temperatures above this range undesirable side reactions occur too rapidly. The ammonolysis of scrap PET to produce terephthalamide appears substantially as follows:

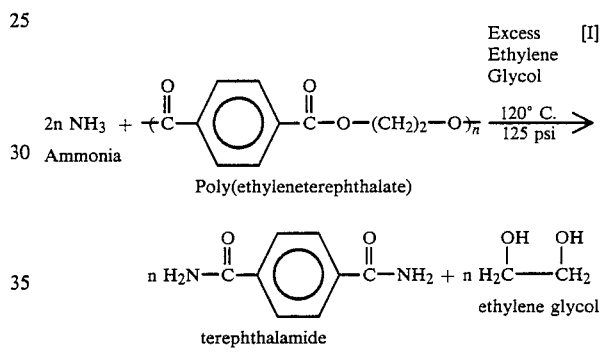

where n is the number of ethyleneterephthalate moieties in a given polymer chain of poly(ethyleneterephthalate). The reaction of a given ethyleneterephthalate moiety of PET with ammonia is represented by the following reaction:

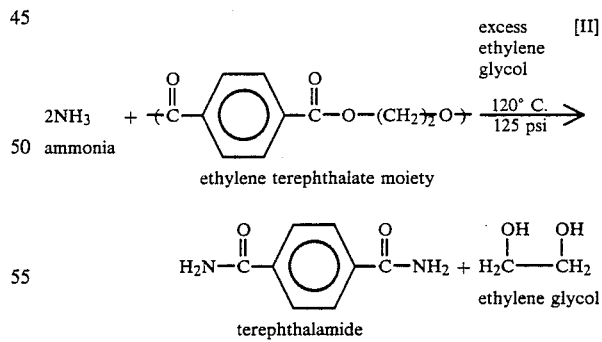

Commercially available PET scrap can be purchased which is substantially free from typical contaminates such as polyethylene bottoms from soft drink bottles, metal caps, and metal rings. These contaminates are often removed by known methods such as grinding the contaminated scrap followed by simple screening and density separation of the contaminates from the PET. Pursuant to the present process, PET is then subjected to substantial ammonolysis to yield terephthalamide and ethylene glycol. The terephthalamide which is insoluble in the ethylene glycol is then separated therefrom by simple filtration to yield terephthalamide in powdered form. Substantially pure terephthalamide can be obtained by washing and filtering the terephthalamide with deionized water and then drying the terephthalamide at elevated temperatures, for example 80° C., for a period of time, for example 1 hour, to produce terephthalamide at yields of greater than 90% and at purities of greater than 99%. The terephthalamide is then further processed by pyrolytic dehydration to produce terephthalonitrile. The ethylene glycol produced during ammonolysis can be sold as a chemical product for various purposes, including, for example, as a monomer for the production of poly(ethyleneterephthalate).

Pyrolytic dehydration of the terephthalamide to produce terephthalonitrile involves transformation of the terephthalamide into terephthalonitrile by the application of heat thereto without oxidation of the terephthalamide. Preferably the diamide, terephthalamide, is heated to a temperature selected from the range of about 250° to about 450° C., more preferably of from about 290° C. to 400° C., and most preferably 340° C. to 370° C., to obtain conversion of the terephthalamide to terephthalonitrile. At temperatures below 250° C. the reaction is slow and at temperature above 450° C. undesirable side reactions occur too rapidly. Most preferably the terephthalamide is heated under conditions which are substantially free of diatomic oxygen to ensure that oxidative reactions involving the terephthalamides or terephthalonitrile do not take place. The pyrolytic dehydration reactions are as follows:

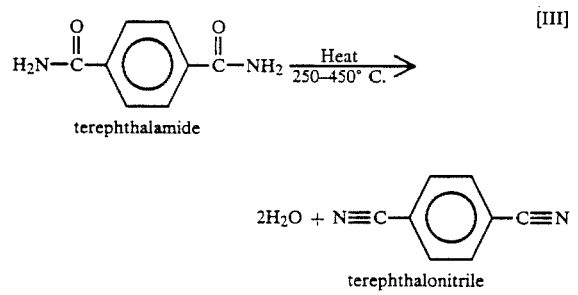

This reaction under the appropriate condition produces good yields of terephthalonitrile from terephthalamide. The terephthalonitrile can then be separated from the unreacted terephthalamide by the addition of a selective solvent thereto. For example, hot ethanol can be employed to dissolve the terephthalonitrile thereby permitting removal of the insoluble terephthalamide by filtration. The terephthalonitrile can then be separated from the solvent by evaporation of the solvent therefrom. If the reaction is substantially complete such that little or no terephthalamide is remaining, then no separation is needed. The resulting terephthalonitrile can then be sold as a raw material or processed further to yield useful products; for example, terephthalonitrile can be processed by hydrogenation to yield useful diamines.

Partial reactions and side reactions are possible during the pyrolytic dehydration of the terephthalamide to the terephthalonitrile. The dehydration of terephthalamide to terephthalonitrile apparently proceeds in two steps. Loss of one molecule of water produces 4-cyanobenzamide as represented by the following reaction sequence:

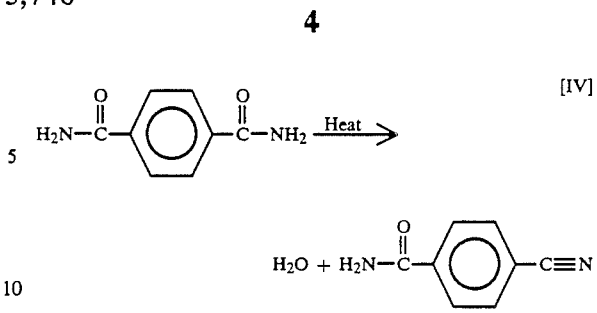

This partial dehydration product can then be converted to terephthalonitrile by the application of additional heat thereto, as represented by the following reaction:

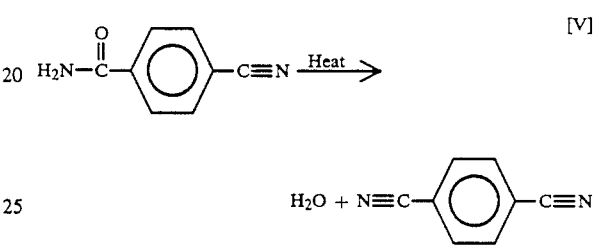

As mentioned above, side reactions are also possible, for example the water generated in the main reaction can react with the partial dehydration product to form 4-cyanobenzoic acid, this possible side reaction is represented as follows:

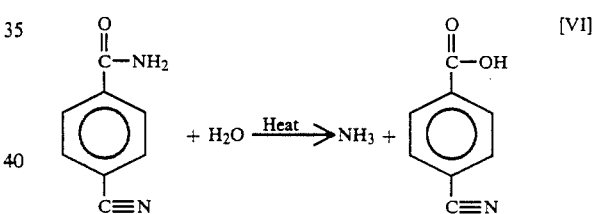

The 4-cyanobenzoic acid side product may be recycled by way of re-amidation to maximize the terephthalonitrile yield. Alternatively its initial formation can be minimized by adding ammonia to the nitrogen heating stream. Possible reaction sequences follow:

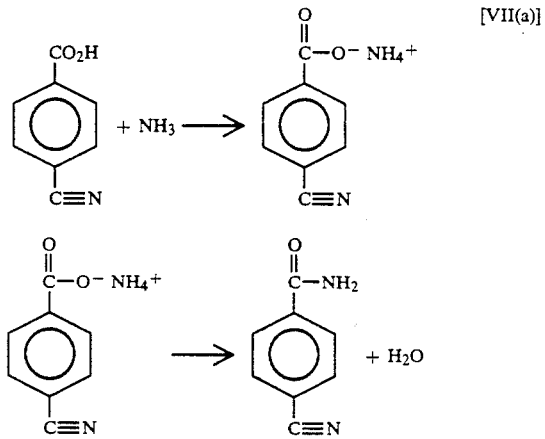

Alternatively:

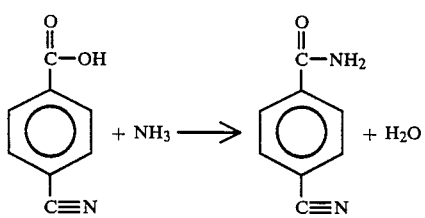

[VII(b)]

The resultant nitrile can then be subjected to pyrolytic dehydration to yield terephthalonitrile as follows:

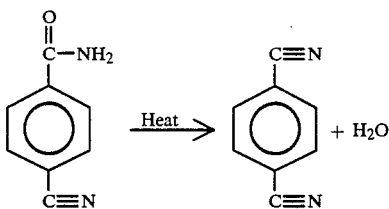

[VIII]

However, one may actually choose to modify the conditions of dehydration to promote the formation of 4-cyanobenzoic acid since it represents a valuable raw material. When 4-cyanobenzoic acid is reduced (hydrogenated) the resultant product is 4-aminomethylbenzoic acid, an attractive bifunctional monomer for the production of polyamide resin. The hydrogenation of 4-cyanobenzoic acid to 4-aminomethylbenzoic acid is represented by the following reaction:

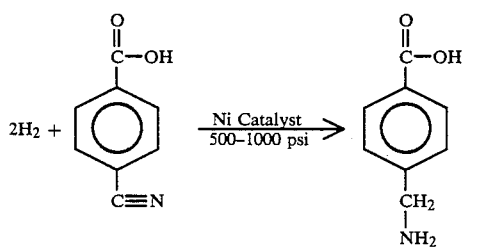

[IX]

The hydrogenation of the terephthalonitrile to produce para-xylylenediamine and/or 1,4-bis(aminomethyl)cyclohexane involves contacting the terephthalonitrile with hydrogen in the presence of an appropriate solvent and a catalyst and applying pressure and heat thereto. One suitable solvent is a blend of ethanol and ammonia having 90% ethanol and 10% ammonia by weight based on the total weight of the solvent. The hydrogen pressure, the time and the temperature employed are determined by the choice of catalyst and the product desired. For example, a nickel catalyst, Ni 5136P, supplied by Harshaw/Filtrol which contains 65% nickel on a silica-alumina support, provides efficient hydrogenation of terephthalonitrile to para-xylylene diamine or 1,4-bis(aminomethyl)cyclohexanes. Hydrogen pressures of 500–1000 psi, a temperature range from 100°–200° C. and a time range from 2–8 hours have produced good yields of desired products. Milder conditions favor xylylene diamines, more stringent conditions favor cyclohexane derivatives.

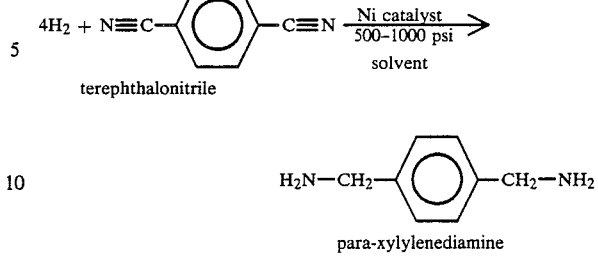

[X]

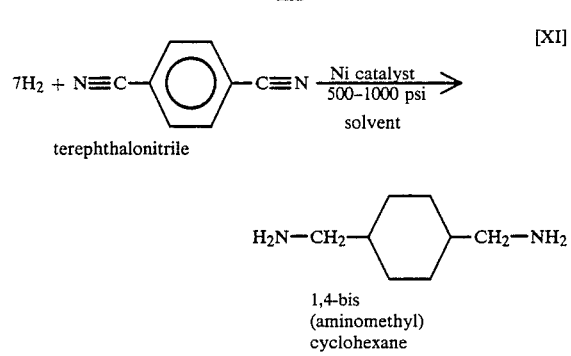

[XI]

From the above process steps it can be seen that high yields of high purity, high value, chemical products such as ethylene glycol, terephthalamide, terephthalonitrile, para-xylylenediamine, 1,4-bis(aminomethyl)cyclohexane and 4-aminomethylbenzoic acid can be obtained from scrap PET by the process of the present invention.

The diamines obtained from the process of the present invention find particular utility as monomers for the production of various polyamide polymers and copolymers. For example, U.S. Pat. No. 4,482,695 discloses polymers derived from para-xylylene diamine. From the above referenced patent which discloses polymers derived from para-xylylenediamine it is evident that the diamines produced by the present process have great potential for utilization in many resins of commercial interest and thus, the process of the present invention has great potential for commercial success due to its ability to convert plentiful, relatively inexpensive PET scrap into relative high value ethylene glycol, diamine and amino acid monomers.

The process is illustrated in the following examples which are not intended to limit the scope of the claims in any manner.

Percent yield is defined as the moles of actual product produced as a percentage of the theoretically maximum number of moles of product producible from the starting material. Thus if 100 moles of starting material can theoretically produce a maximum of 100 moles of product but only 75 moles of product was actually produced then the yield was 75 percent.

EXAMPLE 1

Ammonolysis of Poly(ethyleneterephthalate), PET 100 grams of PET pellets were placed into a 1 liter Parr bomb. 150 grams of ethylene glycol were added to the PET in the Parr bomb. The bomb was sealed and heated to 120° C. Ammonia (anhydrous, liquid) was introduced into the vessel until the pressure equalized with that of the ammonia cylinder (approximately 125 psi). The mixture was then stirred for 7 hrs at 120° C. while maintaining a pressure of 125 psi by continued addition of ammonia. The insoluble terephthalamide was then filtered off from the ethylene glycol and was then washed with 50 mililiters of deionized water. The resulting powder was dried at 80° C. for 1 hour and yielded 79.3 grams of terephthalamide (greater than 90% yield at greater than 99% purity). The results of a substantially identical run are set forth as reaction II of Table 1.

Ammonolysis of PET scrap was also conducted in a process similar to the aforementioned ammonolysis of PET pellets. The PET scrap employed was obtained from PET beverage containers, the walls of which were cut into small strips. These strips of PET were then converted to terephthalamide by ammonolysis. The PET strips were converted to terephthalamide at a faster rate than were the pellets because the strips had greater surface area per gram of PET.

heating the terephthalamide to the reaction temperature, passing nitrogen heated to the reaction temperature through the terephthalamide to remove volatile reaction products, and passing the nitrogen and volatile reaction products through a condenser to condense out the reaction products. Three predominate reaction products were obtained from the condensate. Those products were:

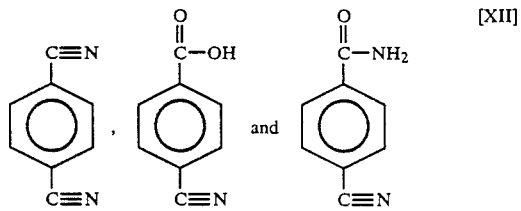

and their respective mole percent yields are listed in the Table II.

TABLE II

| Reaction | Temperature °C. | N2 Flow Rate ML/Min | Time (Hrs) | % YIELD | | |
|---|---|---|---|---|---|---|
| | | | | C≡N—⌬—C≡N | COH—⌬—C≡N | C—NH2—⌬—C≡N |
| X | 290–295 | 350–400 | 5.00 | 2 | 2 | 7 |
| XI | 320–325 | 350–400 | 4.50 | 7 | 8 | 47 |
| XII | 320–325 | 150 | 4.50 | 9 | 9 | 48 |
| XIII | 320–325 | 50–75 | 4.50 | 23 | 23 | 48 |
| XIV | 340–345 | 350–400 | 4.50 | 7 | 9 | 51 |
| XV | 340–345 | 150 | 4.50 | 29 | 44 | 23 |
| XVI | 340–345 | 700 | 1.50 | 9 | 10 | 45 |
| XVII | 340–345 | 700 | 1.50 | 19 | 28 | 50 |
| XVIII | 370–375 | 700 | 1.50 | 20 | 29 | 49 |
| XIX | 370–375 | 700 | 0.25 | 20 | 31 | 49 |

Table I sets forth additional examples (Reactions I-IX) of the conversion of PET to terephthalamide by ammonolysis. The form of the PET, the reaction temperature and the the reaction time were varied to illustrate their impact on yield of terephthalamide.

TABLE I

| Reaction | Form of PET | T °C. | Reaction Time (Hrs) | Yield Terephthalamide |
|---|---|---|---|---|
| I | Pellets | 150 | 3.5 | 91 |
| II | Pellets | 120 | 7.0 | 93 |
| III | Pellets | 180 | 2.0 | 76 |
| IV | Pellets | 180 | 1.0 | 50 |
| V | Pellets | 180 | 3.5 | 77 |
| VI | Bottle Scrap | 150 | 2.0 | 88 |
| VII | Bottle Scrap | 150 | 3.5 | 92 |
| VIII | Bottle Scrap | 180 | 2.0 | 75 |
| IX | Bottle Scrap | 120 | 4.0 | 92 |

EXAMPLE 2

Dehydration of Terephthalamide

The following table (Table II) sets forth the amounts of reaction products obtained at various reaction temperatures, nitrogen flow rates, and reaction periods. Each of the reactions of Table II were conducted by A sand bath was employed to obtain the desired temperatures. A stainless steel reaction vessel and a nitrogen inlet coil were submerged in the sand bath. Terephthalamide was placed on a filter in the reaction vessel. Nitrogen was fed into the coil wherein it was heated to the temperature of the sand bath, the heated nitrogen then entered into the bottom of the reaction vessel wherein it passed through the filter and through the terephthalamide, sweeping out the volatile reaction products. The nitrogen then carried the volatile products out the top of the reaction vessel and into a condenser wherein the volatile reaction products were condensed out from the nitrogen gas stream. Table II indicates the respective yields of products obtained in the condensate.

Table III illustrates the yield of products obtained by the pyrolytic dehydration of the partial reaction product to obtain terephthalonitrile, as illustrated by the following reaction:

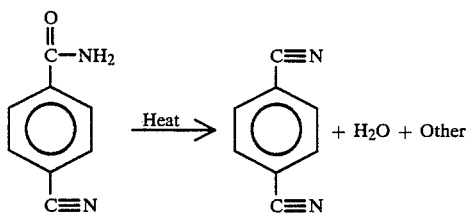
[XIII]

TABLE III

| | | | | % YIELD | | |
|---|---|---|---|---|---|---|
| Reaction | Temperature °C. | N₂ Flow Rate ML/Min | Time (Hrs) | C≡N / C≡N | C≡N / COH | C≡N / C—NH₂ |
| XX | 250 | 100 | 1.00 | 9 | 2 | 71 |
| XXI | 275 | 100 | 1.00 | 18 | 6 | 51 |
| XXII | 300 | 100 | 1.00 | 28 | 9 | 43 |

EXAMPLE 3
Hydrogenation of Terephthalonitrile 5.1 g of terephthalonitrile, 1.0 g of catalyst (Ni 5136P from Harshaw/Filtrol—contains 65% nickel on a silica-alumina support), and about 85 g of ethanol/ammonia (contains about 10 wt % ammonia) were charged to a 300 cc stainless steel pressure reactor. After a nitrogen purge, the vessel was charged to a pressure of 500 to 1000 psi with hydrogen. The temperature was then increased until the reaction temperature of 150° C. had been obtained (typically 20–30 min). After the desired reaction interval, the contents were cooled and sampled. Product analysis and conversion were determined by gas chromatography. Yields of para-xylylenediamine varied between 63–81% depending on hydrogen pressure and reaction time which is preferrably from 2 to 8 hours. The remainder of the product was saturated para-xylylenediamine (1.4 bis (aminomethyl) cyclohexane. Table IV sets forth specific examples of reactions run to obtain the diamines from hydrogenation of terephthalonitrile.

TABLE IV
HYDROGENATION OF TEREPHTHALOY/NITRILE

| Reaction Number | Catalyst | Hydrogen Pressure PSI | Reaction Time Hours | % Yield PXDA | % Yield Side Products |
|---|---|---|---|---|---|
| XXIII | Copper Chromite | 500 | 2 | — | — |
| XXIV | Nickel | 500 | 2 | 63 | 4 1,4 BAC[b] |
| XXV | Nickel | 1000 | 2 | 81 | 1 1,4 BAC |
| XXVI | Nickel | 500 | 2 | 70 | 1 1,4 BAC |
| XXVII | Nickel | 500 | 4 | 36 | 19 1,4 BAC 23 MBA[a] |
| XXVIII | Nickel | 500 | 8 | 76 | 19 1,4 BAC 16 MBA |
| XXIX | Nickel | 2100 | 2 | 73 | 15 MBA |

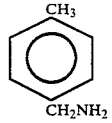

[a]MBA is methylbenzyl amine
[b]1,4 BAC is 1,4 Bis (aminomethyl) cyclohexane
[c]The reaction temperature was 150° C. in all of the reactions (XIII–XXIX) of Table II.

EXAMPLE 4
Hydrogenation of 4-Cyanobenzoic Acid 5 g of 4-cyanobenzoic acid, 1 g of Ni 5136P (nickel catalyst from Harshaw/Filtrol), 85 g of ethanol and 5 g of ammonia were charged to a 300 cc stainless steel pressure vessel. After purging the vessel with nitrogen, it was pressurized to 1000 psi with hydrogen. The temperature was then increased to 150° C. over a period of 30 minutes. The pressure was held at 1000 psi and the temperature at 150° C. for an additional 2.5 hours and then cooled. The product was recovered from the solid precipitate by hot water extraction. The filtered extract (catalyst removed) was evaporated to dryness to yield 3.85 g (75% yield) of a white solid. The infrared spectrum of the white solid was identical to that of an authentic sample of 4-aminomethyl benzoic acid.

I claim:
1. A process for producing 4-aminomethyl benzoic acid from poly(ethyleneterephthalate), said process comprising the steps of:
   (a) ammonolysis of said poly(ethyleneterephthalate) to produce terephthalamide;
   (b) partial pyrolytic dehydration of said terephthalamide to produce 4-cyanobenzoic acid; and
   (c) hydrogenation of said 4-cyanobenzoic acid to produce 4-aminomethylbenzoic acid.

* * * * *